(12) United States Patent
Gavenda et al.

(10) Patent No.: US 7,759,481 B2
(45) Date of Patent: Jul. 20, 2010

(54) SOLID STATE FORMS OF 5-AZACYTIDINE AND PROCESSES FOR PREPARATION THEREOF

(75) Inventors: Ales Gavenda, Lhotka (CZ); Alexandr Jegorov, Dobrá Voda (CZ)

(73) Assignee: Ivax Corporation, Miami, FL (US)

( * ) Notice: Subject to any disclaimer, the term of this patent is extended or adjusted under 35 U.S.C. 154(b) by 110 days.

(21) Appl. No.: 12/008,702

(22) Filed: Jan. 11, 2008

(65) Prior Publication Data

US 2008/0287378 A1 Nov. 20, 2008

Related U.S. Application Data

(60) Provisional application No. 60/880,182, filed on Jan. 11, 2007, provisional application No. 60/880,810, filed on Jan. 16, 2007, provisional application No. 60/933,474, filed on Jun. 5, 2007, provisional application No. 60/998,338, filed on Oct. 9, 2007.

(51) Int. Cl.
*C07H 19/00* (2006.01)
*C07H 19/048* (2006.01)

(52) U.S. Cl. .................... 536/28.2; 536/25.4; 536/28.3; 536/28.4

(58) Field of Classification Search ....................... None
See application file for complete search history.

(56) References Cited

U.S. PATENT DOCUMENTS

| 6,887,855 B2 | 5/2005 | Ionescu et al. |
| 6,943,249 B2 | 9/2005 | Ionescu et al. |
| 7,078,518 B2 | 7/2006 | Ionescu et al. |
| 2006/0247189 A1 | 11/2006 | Ionescu et al. |

*Primary Examiner*—Patrick T Lewis
(74) *Attorney, Agent, or Firm*—Kenyon & Kenyon LLP

(57) ABSTRACT

The present invention provides novel crystalline forms of 5-deazacytidine, and pharmaceutical compositions comprising these novel forms. The invention also provides methods for the preparation of the novel forms and compositions.

20 Claims, 8 Drawing Sheets

SOLID STATE FORMS OF 5-AZACYTIDINE AND PROCESSES FOR PREPARATION THEREOF

RELATED APPLICATIONS

This application claims priority from U.S. provisional application No. 60/880,182 filed Jan. 11, 2007; U.S. provisional application No. 60/880,810 filed Jan. 16, 2007; U.S. provisional application No. 60/933,474 filed Jun. 5, 2007; and U.S. provisional application No. 60/998,338 filed Oct. 9, 2007. The contents of these four applications are incorporated by reference herein, in their entirety and for all purposes.

FIELD OF THE INVENTION

The present invention encompasses solid state forms of 5-azacytidine as well as processes for preparation thereof and pharmaceutical composition thereof.

BACKGROUND OF THE INVENTION

5-Azacytidine, 4-amino-1-β-D-ribofuranosyl-1,3,5-triazin-2(1H)-one, a compound having the chemical structure,

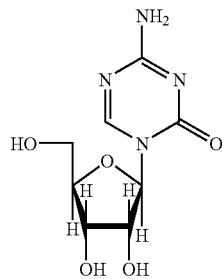

is an antineoplastic drug exhibiting activity against, e.g., leukemia, lymphoma and various solid tumours. 5-Azacytidine acts also as an inhibitor of DNA methyltransferase and was approved for the treatment of myelodispactic syndromes, a family of bone-marrow disorders. It is being marketed under the name Vidaza by Pharmion.

Crystallization of 5-azacytidine providing a methanol solvate of 5-azacytidine and crystallization of 5-azacytidine hydrate were described by Pískala and Šorm (Nucleic acid chemistry, Improved and new synthetic procedures, methods and techniques, Part one, L. B. Townsend and R. S. Tipson, Eds., Wiley Inc., New York, 1978, pp. 435-441).

U.S. Pat. No. 6,943,249 ("'249") claims in claim 1 preparation of form I by recrystallization of 5-azacytidine from a solvent mixture comprising at least one primary solvent and at least one co-solvent selected from the group consisting $C_2$-$C_5$ alcohols, aliphatic ketones, and alkyl cyanides, by cooling said solvent mixture from a temperature selected to allow said 5-azacytidine to dissolve completely to about ambient temperature, and isolating the recrystallized 5-azacytidine. The US '249 patent also claims in claim 11 a method for preparing Form I comprising recrystallizing 5-azacytidine from a solvent mixture comprising at least one primary solvent and at least one co-solvent selected from the group consisting $C_3$-$C_5$ alcohols and alkyl cyanides, by cooling said solvent mixture from a temperature selected to allow said 5-azacytidine to dissolve completely to about −20° C., and isolating the recrystallized 5-azacytidine" also leads to form I of 5-azacytidine. All of the examples of the '249 patent use DMSO as a solvent to which a co-solvent is added. The '249 patent also describes form I having the most prominent 2 theta angles at 12.182, 13.024, 14.399, 16.470, 18.627, 19.049, 20.182, 21.329, 23.033, 23.872, 26.863, 27.1735, 29.277, 29.591, 30.369, and 32.072.

U.S. Pat. No. 6,887,855 discloses eight polymorphic forms of 5-azacytidine, denominated Forms I-VIII, for which Forms I-III are reported to be in the prior art. The characterization of each of these forms in U.S. Pat. No. 6,887,855 is incorporated herein by reference.

U.S. Pat. No. 6,887,855 ("'855") discloses the synthesis and isolation of Form I, where the obtained form I is reported to be characterized by the same most prominent two theta angles as described in the '249 patent and by FIG. 1. The '855 patent discloses also a mixture of 5-azacytidine form I and a form identified by the most prominent two theta angles at 13.5, 17.6, and 22.3 degrees two-theta, denominated form II.

U.S. Pat. No. 6,887,855 also reports additional crystalline forms of 5-azacytidine, denominated Form IV having the most prominent 2 theta angles at 5.704, 11.571, 12.563, 14.070, 15.943, 16.993, 18.066, 20.377, 20.729, 21.484, 21.803, 22.452, 22.709, 23.646, 24.068, 25.346, 25.346, 26.900, 27.991, 28.527, 28.723, 30.124, 30.673, 31.059, 35.059, 38.195 and 38.403; Form V having the most prominent 2 theta angles at 11.018, 12.351, 13.176, 13.747, 14.548, 15.542, 16.556, 17.978, 18.549, 19.202, 19.819, 20.329, 21.518, 21.970, 22.521, 23.179, 24.018, 24.569, 27.224, 28.469, 29.041, 29.429, 30.924, 31.133 and 37.938; Form VI, a mixture of form I and a crystalline form which exhibits distinctive peaks at 5.8, 11.5, 12.8, 22.4, and 26.6 degrees two-theta, denominated Form VII; a crystalline form having the most prominent two theta angles at 6.599, 10.660, 12.600, 13.358, 15.849, 17.275, 20.243, 20.851, 21.770, 22.649, 25.554, 25.740, 29.293, 32.148, 35.074, and 38.306 degrees two-theta, denominated Form VIII; as well as an amorphous form, processes for preparation thereof, and conversion of form I to the crystalline form having most prominent diffractions on PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta, denominated Form III, and to amorphous form.

According to U.S. Pat. No. 7,078,518 (a divisional of the '855 patent), 5-azacytidine Forms IV, V, VI, and mixtures of form I and VII, are prepared by recrystallization processes that include dissolving 5-azacytidine in dimethylsulfoxide, and at least one co solvent is added to the solution of 5-azacytidine facilitating the crystallization; wherein the co solvents is toluene, methanol or chloroform.

The present invention relates to the solid-state physical properties of 5-azacytidine as well as to processes for preparation thereof.

These properties can be influenced by controlling the conditions under which 5-azacytidine is obtained in solid form. Solid-state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid-state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid-state form of a compound may also affect its behavior on compaction and its storage stability.

These practical physical characteristics are influenced by the conformation and orientation of molecules in the unit cell, which defines a particular polymorphic form of a substance that can be identified unequivocally by X-ray spectroscopy. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by solid-state $^{13}$C NMR spectrometry and infrared spectroscopy.

The present invention also relates to solvates of 5-azacytidine. When a substance crystallizes out of solution, it may trap molecules of solvent at regular intervals in the crystal lattice. Solvation also affects utilitarian physical properties of the solid-state like flowability and dissolution rate.

One of the most important physical properties of a pharmaceutical compound, which can form polymorphs or solvates, is its solubility in aqueous solution, particularly the solubility in gastric juices of a patient. Other important properties relate to the ease of processing the form into pharmaceutical dosages, as the tendency of a powdered or granulated form to flow and the surface properties that determine whether crystals of the form will adhere to each other when compacted into a tablet.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

SUMMARY OF THE INVENTION

In one embodiment, the present invention provides crystalline 5-azacytidine characterized by data selected from a group consisting of: a PXRD pattern with peaks at about 12.2, 13.1, 14.4, 16.2, and 23.1±0.2 degrees two-theta, a PXRD pattern as depicted in FIG. 11, and combination thereof containing less than about 5% by weight of a crystalline form having most prominent diffractions at PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta and less than about 5% by weight of a crystalline form with having most prominent PXRD diffractions at 13.4, 17.6, and 22.1 degrees two-theta.

In another embodiment, the present invention encompasses 5-azacytidine containing about 10 ppm to about 2000 ppm of non-volatile solvents. Preferably, the 5-azacytidine is crystalline 5-azacytidine characterized by data selected from a group consisting of: a PXRD pattern with peaks at about 12.2, 13.1, 14.4, 16.2, and 23.1±0.2 degrees two-theta, a PXRD pattern as depicted in FIG. 11, and combination thereof, having less than about 5% by weight of a crystalline form having most prominent diffractions at PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta and less than about 5% by weight of a crystalline 5-azacytidine having most prominent PXRD diffractions at 13.4, 17.6, and 22.1 degrees two-theta.

In yet another embodiment, the present invention provides a process for preparing 5-azacytidine containing about 10 ppm to about 2000 ppm of non volatile solvents comprising heating a suspension of 5-azacytidine in a single solvent selected from a group consisting of: aliphatic alcohol, nitrile, ether, nitromethane, and pyridine, or in a mixture of solvents comprising the above single solvent and a non-polar organic solvent selected from a group consisting of ketone and ester, and recovering the obtained 5-azacytidine containing about 10 ppm to about 2000 ppm of non volatile solvents; wherein the single polar solvent or its mixture with a non-polar solvent has boiling point of less than 140° C. Preferably, the obtained 5-azacytidine is crystalline 5-azacytidine characterized by data selected from a group consisting of: a PXRD pattern with peaks at about 12.2, 13.1, 14.4, 16.2, and 23.1±0.2 degrees two-theta, a PXRD pattern as depicted in FIG. 11, and combination thereof, containing less than about 5% by weight of a crystalline 5-azacytidine characterized having most prominent diffractions at PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta and less than about 5% by weight of a crystalline 5-azacytidine having most prominent PXRD diffractions at t 13.4, 17.6, and 22.1 degrees two-theta.

In one embodiment, the present invention provides crystalline 5-azacytidine characterized by data selected from a group consisting of: a powder XRD pattern with peaks at about 8.7, 9.5, 12.1, 14.4, and 17.3±0.2 degrees two-theta, a PXRD pattern as depicted in FIG. 1; a solid-state $^{13}$C NMR spectrum having signals with chemical shifts at about 166.2, 155.9, and 154.2±0.2 ppm; a solid-state $^{13}$C NMR spectrum as depicted in FIG. 2; a solid-state $^{13}$C NMR spectrum having chemical shift differences between the signal exhibiting the lowest chemical shift and others in the chemical shift range of 90 to 180 ppm of about 60.5, 62.2, and 72.5±0.1 ppm, and combination thereof.

In another embodiment, the present invention provides a process for the preparation of crystalline 5-azacytidine characterized by data selected from a group consisting of: a powder XRD pattern with peaks at about 8.7, 9.5, 12.1, 14.4, and 17.3±0.2 degrees two-theta, a PXRD pattern as depicted in FIG. 1; a solid-state $^{13}$C NMR spectrum having signals with chemical shifts at about 166.2, 155.9, and 154.2±0.2 ppm; a solid-state $^{13}$C NMR spectrum as depicted in FIG. 2; a solid-state $^{13}$C NMR spectrum having chemical shift differences between the signal exhibiting the lowest chemical shift and others in the chemical shift range of 90 to 180 ppm of about 60.5, 62.2, and 72.5±0.1 ppm, and combination thereof, comprising providing a solution of 5-azacytidine in N-methylpyrrolidone (referred to as NMP), and precipitating the said crystalline by cooling to a temperature of about 20° C. to about 0° C. to obtain a suspension comprising of the said crystalline form.

In one embodiment, the present invention provides solvated forms of 5-azacytidine selected from a group consisting of: 1,3-dimethyl-2-imidazolidinone solvate; and 1,3-dimethyl-3,4,5,6-tetrahydro-2(1H)-pyrimidinone solvate.

In another embodiment, the present invention provides crystalline 5-azacytidine characterized by data selected from the group consisting of: a powder XRD pattern with peaks at about 5.8, 11.6, 12.8, 16.2, and 17.4±0.2 degrees two-theta; a PXRD pattern as depicted in FIG. 3; a single crystal XRD with the following data: monoclinic crystal system; unit cell parameters: a, b, c: a=5.14 Å, b=7.78 Å, c=15.40 Å, alpha=90°, beta=99.60°, and gamma=90°, respectively; an ORTEP view of a single crystal as depicted in FIG. 5; a solid-state $^{13}$C NMR spectrum having signals with chemical shifts at about 167.3, 156.2, and 93.4±0.2 ppm; a solid-state $^{13}$C NMR spectrum as depicted in FIG. 4; a solid-state $^{13}$C NMR spectrum having chemical shift differences between the signal exhibiting the lowest chemical shift and another in the chemical shift range of 90 to 180 ppm of about 62.8 and 73.9±0.1 ppm, and combination thereof containing less than about 20% by weight of crystalline 5-azacytidine having the most prominent 2 theta angles at 12.182, 13.024, 14.399, 16.470, 18.627, 19.049, 20.182, 21.329, 23.033, 23.872, 26.863, 27.1735, 29.277, 29.591, 30.369, and 32.072.

In yet another embodiment, the present invention provides crystalline 5-azacytidine characterized by data selected from a group consisting of: a powder XRD pattern with peaks at about 8.5, 9.4, 12.0, 14.4, 17.1 and 31.3±0.2 degrees two-theta; a PXRD pattern as depicted in FIG. 7; a solid-state $^{13}$C NMR spectrum having signals with chemical shifts at about 166.0, 153.9, and 93.4±0.2 ppm; a solid-state $^{13}$C NMR spectrum as depicted in FIG. 8; a solid-state $^{13}$C NMR spectrum having chemical shift differences between the signal exhibiting the lowest chemical shift and another in the chemical shift range of 90 to 180 ppm of about 60.5 and 72.6±0.1 ppm, and combination thereof.

In one embodiment, the present invention provides crystalline 5-azacytidine characterized data selected from a group consisting of: a powder XRD pattern with peaks at about 9.4, 11.8, 12.1, 14.3 and 16.5±0.2 degrees two-theta; a PXRD pattern as depicted in FIG. 9; a solid-state $^{13}$C NMR spectrum having signals with chemical shifts at about 166.6, 154.3, and 93.9±0.2 ppm; a solid-state $^{13}$C NMR spectrum having signals with chemical shifts at about 166.6, 155.8, and 93.9±0.2 ppm; a solid-state $^{13}$C NMR spectrum as depicted in FIG. 10; a solid-state $^{13}$C NMR spectrum having chemical shift differences between the signal exhibiting the lowest chemical shift and another in the chemical shift range of 90 to 180 ppm of about 60.4 and 72.7±0.1 ppm, a solid-state $^{13}$C NMR spectrum having chemical shift differences between the signal exhibiting the lowest chemical shift and another in the chemical shift range of 90 to 180 ppm of about 61.9 and 72.7±0.1 ppm, and combination thereof.

In another embodiment, the present invention provides crystalline 5-azacytidine characterized by data selected from the group consisting of: a powder XRD pattern with peaks at about 11.0, 12.4, 13.7, 16.5, and 18.5±0.2 degrees two-theta; a PXRD pattern as depicted in FIG. 11, and combination thereof containing less than about 20% by weight of crystalline 5-azacytidine having the most prominent 2 theta angles at 12.182, 13.024, 14.399, 16.470, 18.627, 19.049, 20.182, 21.329, 23.033, 23.872, 26.863, 27.1735, 29.277, 29.591, 30.369, and 32.072.

In yet another embodiment, the present invention encompasses a pharmaceutical composition comprising any one of the above forms of 5-azacytidine, and at least one pharmaceutically acceptable excipient; wherein the starting 5-azacytidine includes also 5-azacytidine containing about 10 ppm to about 2000 ppm of non-volatile solvents.

In one embodiment, the present invention encompasses a pharmaceutical composition comprising any one of the above forms of 5-azacytidine prepared according to the processes of the present invention, and at least one pharmaceutically acceptable excipient; wherein the starting 5-azacytidine includes also 5-azacytidine containing about 10 ppm to about 2000 ppm of non-volatile solvents.

In another embodiment, the present invention encompasses a process for preparing a pharmaceutical formulation comprising combining any one of the above forms of 5-azacytidine with at least one pharmaceutically acceptable excipient; wherein the 5-azacytidine includes also 5-azacytidine containing about 10 ppm to about 2000 ppm of non-volatile solvents.

In yet another embodiment, the present invention encompasses a process for preparing a pharmaceutical composition comprising any one of the above forms of 5-azacytidine, prepared according to the processes of the present invention, and at least one pharmaceutically acceptable excipient; wherein the 5-azacytidine includes also 5-azacytidine containing about 10 ppm to about 2000 ppm of non-volatile solvents.

In one embodiment, the present invention encompasses the use of any one of the above forms of 5-azacytidine, for the manufacture of a pharmaceutical composition; wherein the 5-azacytidine includes also 5-azacytidine containing about 10 ppm to about 2000 ppm of non-volatile solvents.

DETAILED DESCRIPTION OF THE INVENTION

The present invention provides different solid state forms of 5-azacytidine, as well as 5-azacytidine having low residual solvent level of non-volatile solvents, methods for preparation thereof, and pharmaceutical compositions comprising thereof.

The presence of residual non-volatile solvents in the forms of 5-azacytidine in the prior art, particularly in Form I of 5-azacytidine, is despite a final step of vacuum drying. This contamination with non-volatile solvent is a particular problem for 5-azacytidine because it is sparingly soluble in most solvents other than non-volatile solvents, requiring use of these non-volatile solvents for production. Further, many of the polymorphic forms present in the prior art occur as a multi-phase of multiple crystal forms, which is not suitable for pharmaceutical formulation.

As used herein, the term "solvate" refers to a crystalline substance that includes any solvent other than water at levels of more than 1% by weight, as determined by GC or NMR.

As used herein, the term chemical shift difference refers to the difference in chemical shifts between a reference signal and another signal in the same solid-state $^{13}$C NMR spectrum. In the present patent application the chemical shift differences were calculated by subtracting the chemical shift value of the signal exhibiting the lowest chemical shift (reference signal) in the solid-state $^{13}$C NMR spectrum in the range of 90 to 180 ppm from chemical shift values of another (observed) signals in the same solid-state NMR spectrum in the range of 90 to 180 ppm. These chemical shift differences are to provide a measurement for a substance, for example 5-azacytidine, of the present invention compensating for a phenomenon in NMR spectroscopy wherein, depending on the instrumentation, temperature, and calibration method used, a shift in the solid-state NMR "fingerprint" is observed. This shift in the solid-state NMR "fingerprint", having signals at certain positions, is such that although the individual chemical shifts of signals have altered, the difference between chemical shifts of each signal and another is retained.

Figure 1:
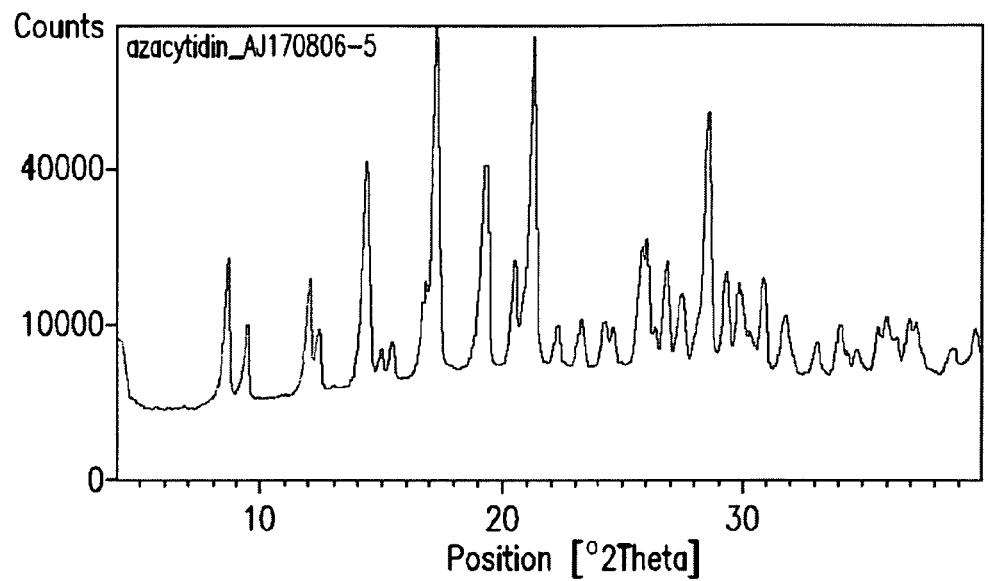
FIG. 1 illustrates a powder X-ray diffraction pattern of crystalline 5-azacytidine Form IX.

The PXRD diffractogram of form I disclosed in FIG. 1 of U.S. Pat. No. 6,887,855 shows the presence of peaks of form III at approximately 6.6, 15.1 and 17.4 degrees two-theta. Thus, the disclosed form I is actually a mixture of form I and III. Form I contains about 5% by weight of form III. The content of form III can be measured by PXRD using the peak at 15.1 degrees two-theta.

Figure 11:
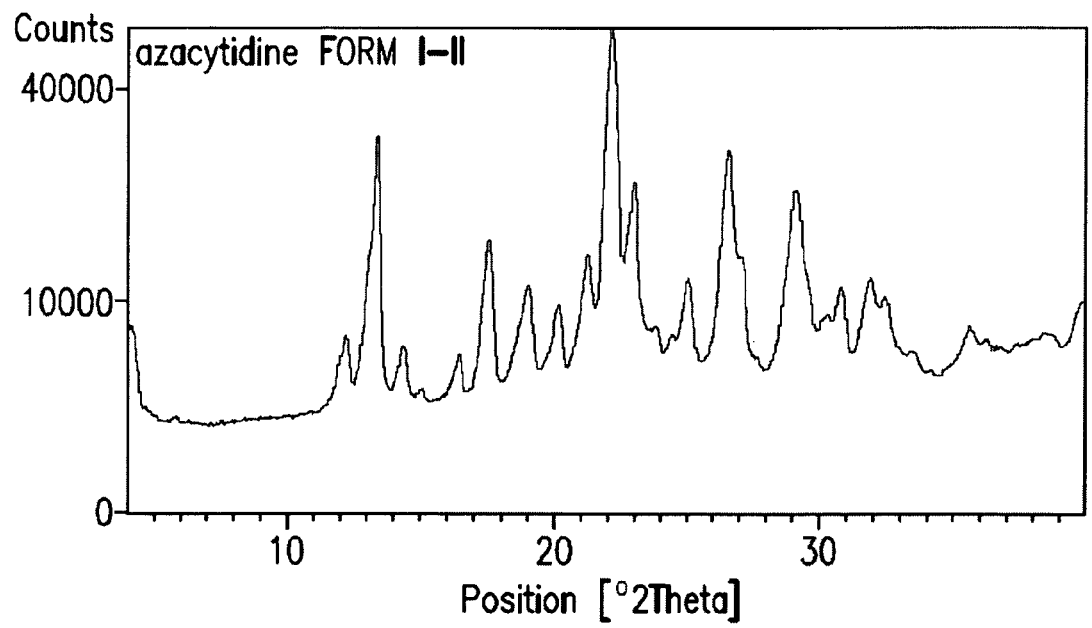
FIG. 11 illustrates a powder X-ray diffraction pattern of pure crystalline 5-azacytidine Form V.
Figure 12:
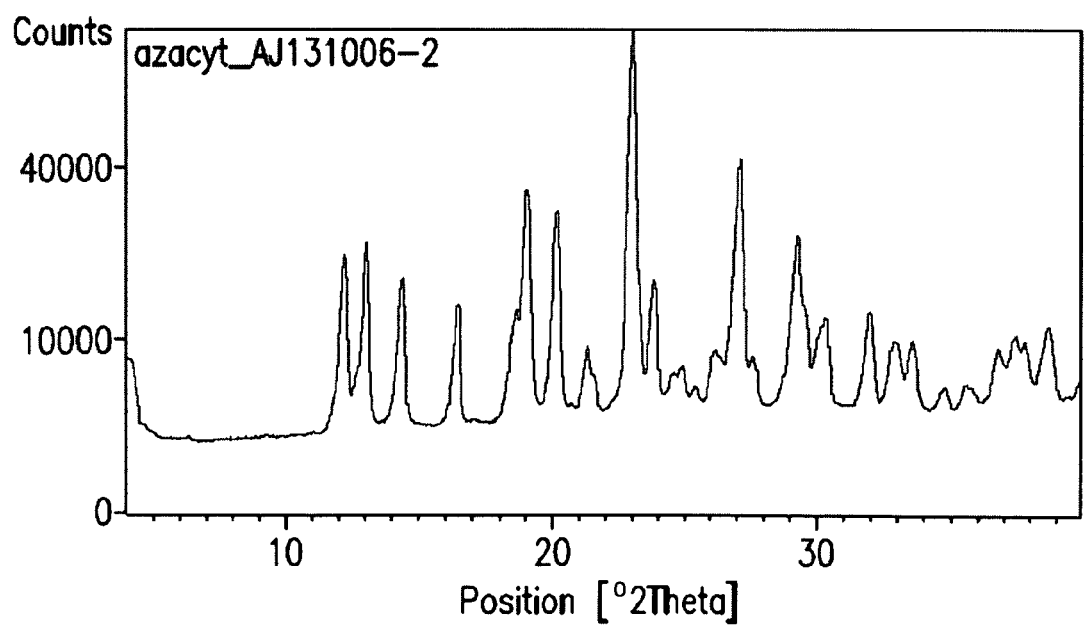
FIG. 12 illustrates a powder X-ray diffraction pattern for crude commercial 5-azacytidine containing about 80% of form II and 20% of form I.

The present invention provides crystalline 5-azacytidine characterized by data selected from a group consisting of: a PXRD pattern with peaks at about 12.2, 13.1, 14.4, 16.2, and 23.1±0.2 degrees two-theta, a PXRD pattern as depicted in FIG. 11, and combination thereof, designated pure form I, containing less than about 5% by weight of a crystalline form having most prominent diffractions at PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta, designated form III, and less than about 5% by weight of a crystalline 5-azacytidine with having most prominent PXRD diffractions at 13.4, 17.6, and 22.1±0.2 degrees two-theta, designated form II. This form can be identified as "pure form I" or "pure crystalline form I".

Preferably, pure form I contains less than about 4%, 3%, 2%, or preferably less than about 1% by weight of form III, and less than about 4%, 3%, 2%, or preferably less than about 1% by weight of form II. The content of form III in pure form I can be measured by PXRD using any one of the peaks at 6.6, 15.1 and 17.4±0.2 degrees two-theta. For example, FIG. 1 of U.S. Pat. No. 6,887,855 shows peaks at 15.1 and 17.4 degrees two-theta. The content of form II in pure form I can be measured by PXRD using any one of the peaks at 13.4, 17.6, and 22.1±0.2 degrees two-theta.

The pure form I of the present invention can be further characterized by a powder XRD pattern with peaks at about 19.1, 20.2, 27.1, 29.3, and 32.1±0.2 degrees two-theta.

The above pure crystalline form I is also characterized by polymorphic homogeneity and crystal uniformity.

The present invention also provides 5-azacytidine containing about 10 ppm to about 2000 ppm of non-volatile solvents, more preferably about 10 to about 500 ppm. Preferably, the 5-azacytidine is pure crystalline form I of 5-azacytidine.

As used herein, the term "non-volatile solvents" refers to organic solvents having a boiling point of at least 140° C. Examples for such solvents include but not limited to DMSO, formamide, DMF, DMA, NMP, and others.

The present invention also relates to a method of preparing 5-azacytidine containing about 10 ppm to about 2000 ppm, more preferably about 10 to about 500 ppm of non-volatile solvents. The method comprises heating a suspension of 5-azacytidine in a single polar organic solvent selected from a group consisting of: aliphatic alcohol, nitrile, ether, nitromethane, pyridine, or in a mixture of solvents comprising the said polar organic solvent and a non-polar organic solvent selected from a group consisting of: ketone, a hydrocarbon, or ester, and recovering 5-azacytidine containing about 10 ppm to about 2000 ppm of non-volatile solvents; wherein the single polar solvent or its mixture with a non-polar solvent has boiling point of less than 140° C. Preferably, the obtained 5-azacytidine is pure crystalline form I of 5-azacytidine.

The suspension of 5-azacytidine is provided by combining 5-azacytidine and a single polar organic solvent or a mixture of solvents comprising the said polar organic solvent and a non-polar organic solvent.

Preferably, the aliphatic alcohol is a $C_{2-6}$ aliphatic alcohol, more preferably, methanol, ethanol, 2-propanol, 1-propanol, 1-butanol, 2-butanol, i-butanol, amylalcohol, methoxyethanol, ethoxyethanol or mixtures thereof, most preferably, either 1-butanol or ethanol. Preferably, the nitrile is $C_{2-4}$ nitrile, more preferably, acetonitrile. Preferably, the ether is a $C_{3-8}$ ether, including penta or hexa-cyclic ether, more preferably, dimethoxyethane, tert-butylmethylether, dioxolane, tetrahydrofurane, methyl-tetrahydrofurane, or dioxane. Most preferably, the ether is 1,4-dioxane. Preferably, the single polar organic solvent is either ethanol or 1-butanol.

Preferably, the ketone is $C_{3-6}$ ketone, more preferably, acetone, methylethylketone, or methylbutylketone, most preferably, either methylethyl ketone or methylisobutyl ketone. Preferably, the ester is $C_{2-6}$ ester, more preferably, ethylacetate, propyl acetate, isopropyl acetate, butylacetate, isobutylacetate, most preferably ethylacetate. Preferably the hydrocarbon is a $C_{6-10}$ hydrocarbon, more preferably hexane, heptane, cyclohexane, methylcyclohexane, toluene, m-xylene, p-xylene, or chlorobenzene, most preferably toluene.

Preferably, the solvent used to prepare the suspension is a single polar organic solvent, more preferably, either ethanol or 1-butanol.

The suspension is, preferably, heated to a temperature of about 30° C. to about 130° C., more preferably to a temperature of about 60° C. to about 120° C. The heating is done, preferably, under stirring. Heating the suspension of 5-azacytidine may be done under inert atmosphere. Preferably, the inert atmosphere is obtained by using nitrogen.

Optionally the hot suspension may be seeded with 5-azacytidine crystalline form I to facilitate the rate of crystallization of 5-azacytidine crystalline form I.

The recovery of the obtained 5-azacytidine may be accomplished for example by cooling the heated suspension; filtering the cooled suspension; washing the filtered precipitate and drying. Preferably, the heated suspension is cooled to a temperature of about 30° C. to about 20° C. Drying may be carried out at any suitable temperature, such as about 20° C. to about 50° C.

Figure 2:
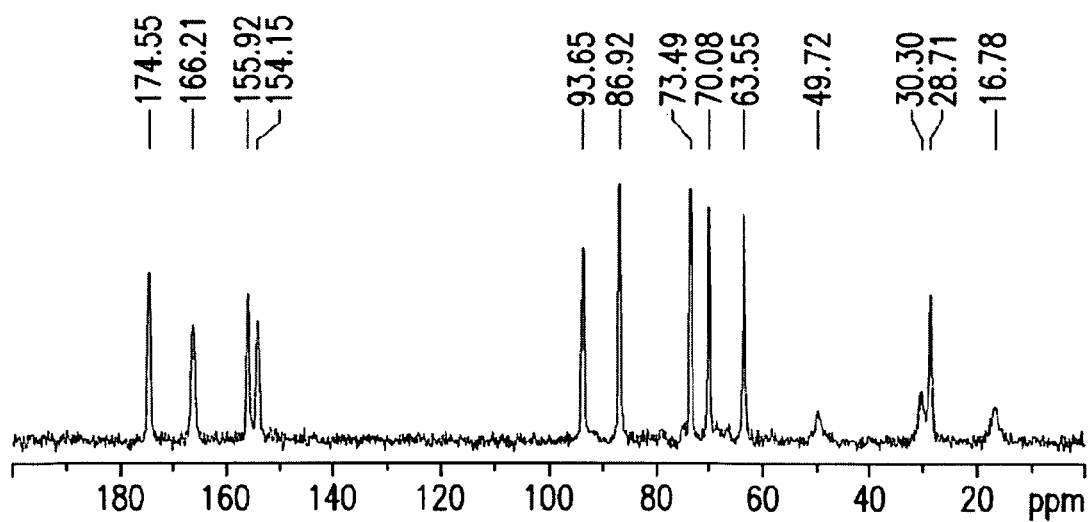
FIG. 2 illustrates a solid-state $^{13}$C NMR spectrum of crystalline 5-azacytidine form IX.

The present invention provides crystalline 5-azacytidine characterized by data selected from a group consisting of: a powder XRD pattern with peaks at about 8.7, 9.5, 12.1, 14.4 and 17.3±0.2 degrees two-theta; a PXRD pattern as depicted in FIG. 1; a solid-state $^{13}$C NMR spectrum having signals with chemical shifts at about 166.2, 155.9, and 154.2±0.2 ppm; a solid-state $^{13}$C NMR spectrum as depicted in FIG. 2; a solid-state $^{13}$C NMR spectrum having chemical shift differences between the signal exhibiting the lowest chemical shift and another in the chemical shift range of 90 to 180 ppm of about 60.5, 62.2, and 72.5±0.1 ppm, and combination thereof. The signal exhibiting the lowest chemical shift in the chemical shift range of 90 to 180 ppm is typically at about 93.7±1 ppm. This form can be designated "Form IX" or crystalline form IX".

The crystalline Form IX may be further characterized by a powder XRD pattern with peaks at about 19.4, 21.3, and 28.6±0.2 degrees two-theta. In addition, the crystalline may be further characterized by a solid-state $^{13}$C NMR spectrum having signals with chemical shifts at about 86.9, and 73.5±0.2 ppm.

Furthermore, the crystalline Form IX may be additionally characterized by a solid-state $^{13}$C NMR spectrum having signals with chemical shifts at about 174.6 and 28.7±0.2 ppm.

The above crystalline Form IX is a solvated form of 5-azacytidine, preferably an N-methylpyrrolidone solvate, more preferably, a mono-N-methylpyrrolidone solvate. Preferably, the ratio of NMP to 5-azacytidine, as determined by solution $^1$H NMR analysis is 1:1 (molecular ratio).

Furthermore, the crystalline Form IX can be characterized by any other method known to a skilled artisan, such as, for example, FTIR, and Raman Spectroscopy.

The above form crystallizes in well developed crystals and thus, can be easily recovered by filtration. The well defined crystals also contribute to a smaller surface area and thus, to lower absorption of impurities from the mother liquor when precipitated.

The above crystalline form IX has less than about 10%, preferably less than about 5%, more preferably less than about 1% by weight of crystalline 5-azacytidine form III or crystalline 5-azacytidine having the most prominent two theta angles at 6.599, 10.660, 12.600, 13.358, 15.849, 17.275, 20.243, 20.851, 21.770, 22.649, 25.554, 25.740, 29.293, 32.148, 35.074, and 38.306 degrees two-theta, denominated Form VIII. The content of form III can be measured by PXRD using any one of the peaks of form III at 6.6, 13.1, 22.8 and 31.4 degrees two-theta. The content of form VIII can be measured by PXRD using any one of the peaks at 6.6, 12.6, 21.8 and 22.7±0.2 degrees two-theta.

The process for preparation of Form IX comprises providing a solution of 5-azacytidine in N-methylpyrrolidone (referred to as NMP), and precipitating the crystalline 5-azacytidine by cooling to a temperature of about 20° C. to about 0° C. to obtain a suspension comprising the crystalline form IX.

Preferably, the solution is provided by combining 5-azacytidine and NMP and heating the combination. Heating can be carried out to a temperature of about 50° C. to reflux temperature, more preferably to about 70° C. to about 100° C., and most preferably to about 90° C.

The ratio of 5-azacytidine to NMP is preferably from about 1:8 to about 1:20, more preferably, from about 1:8 to about 1:12 w/v, respectively.

Optionally, the solution of 5-azacytidine in NMP can include a second solvent. The second solvent can be selected from, but not limited to a $C_3$-$C_8$ ketone such as methylethyketone or a $C_5$-$C_{12}$ aromatic or saturated hydrocarbon such as toluene.

Preferably, the precipitation is done by cooling the solution to a temperature of about 10° C. to about 0° C.

The process for preparing the above crystalline form IX of 5-azacytidine can further comprise a recovery process. Preferably, the recovery is done by filtering the suspension, washing the filtered crystalline and drying it. Drying may be carried out at any suitable temperature, such as about 20° C. to about 50° C.

The present invention also provides solvated forms of 5-azacytidine selected from a group consisting of: 1,3-dimethyl-2-imidazolidinone solvate and 1,3-dimethyl-3,4,5,6-tetrahydro-2(1H)-pyrimidinone solvate.

Figure 7:
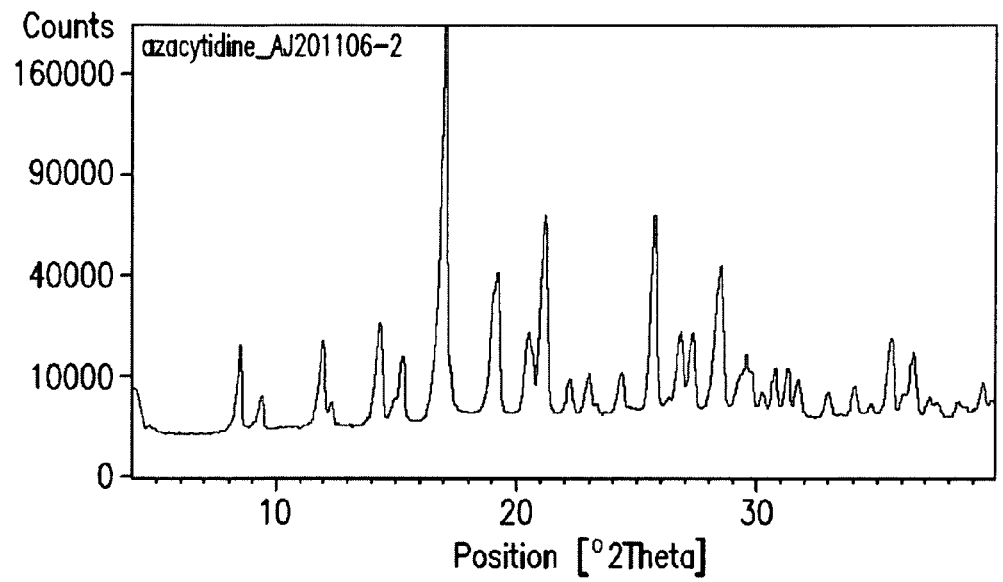
FIG. 7 illustrates a powder X-ray diffraction pattern of crystalline 5-azacytidine Form XI.

The PXRD diffractogram of form VII disclosed in FIG. 7 of U.S. Pat. No. 7,078,518 shows that the mixture of form I and form VII has about 60% by weight of form I. The content of form I can be measured by PXRD using the peak at about 20.2±0.2 degrees two-theta.

Figure 3:
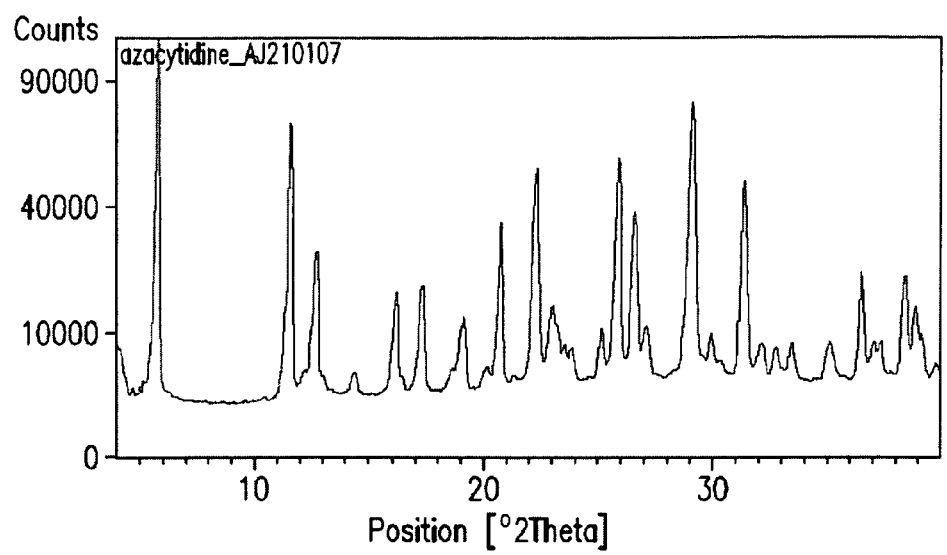
FIG. 3 illustrates a powder X-ray diffraction pattern for pure crystalline 5-azacytidine Form VII.
Figure 4:
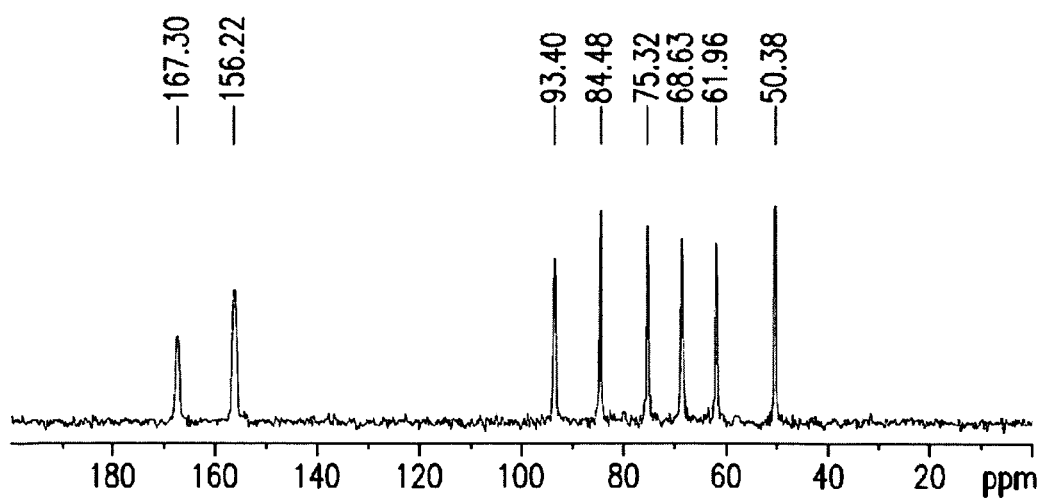
FIG. 4 illustrates a solid-state $^{13}$C NMR spectrum of pure crystalline 5-azacytidine Form VII.
Figure 5A:
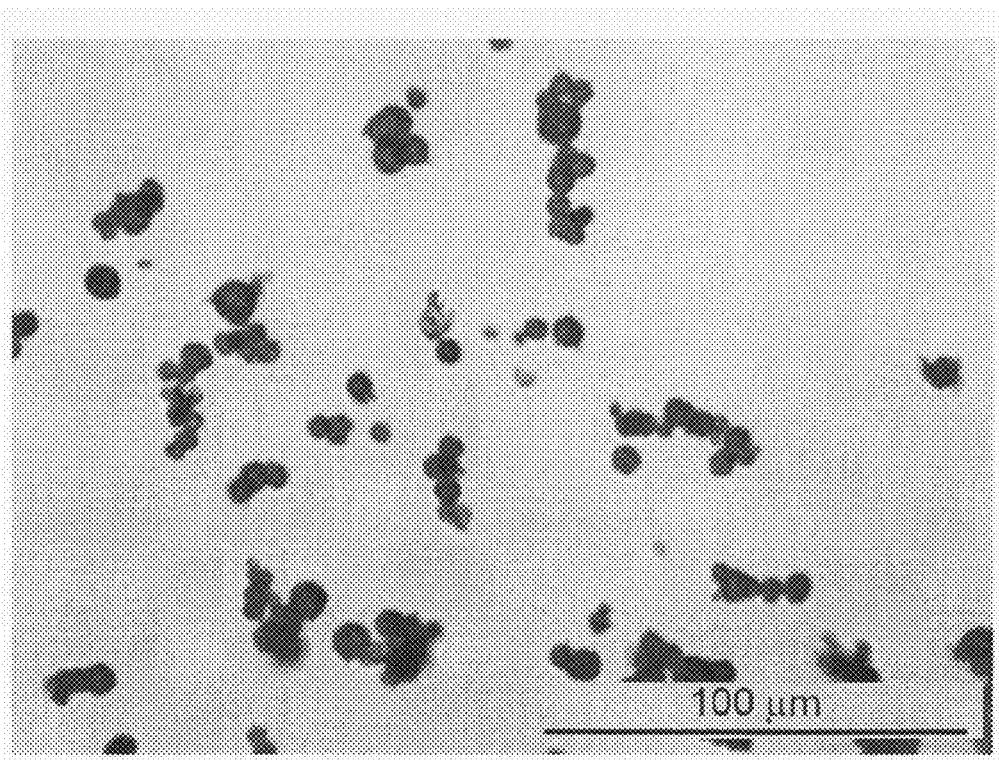
FIG. 5 illustrates microscopic views of pure crystalline 5-azacytidine form VII (FIG. 5a), and of pure crystalline form I (FIG. 5b).
Figure 5B:
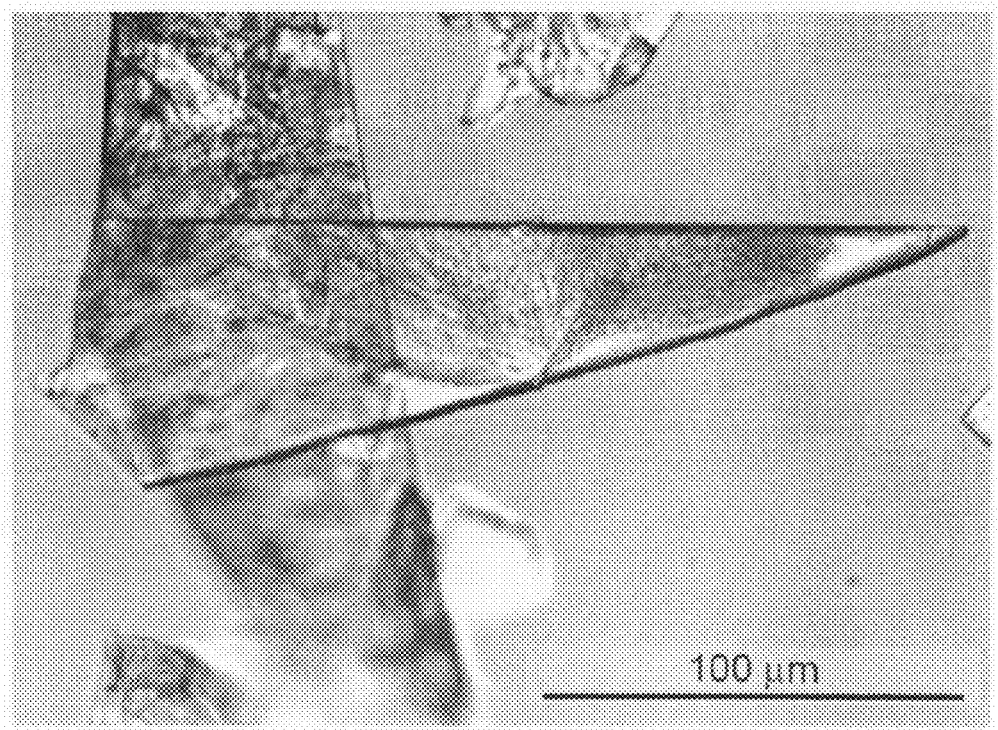

The present invention provides crystalline 5-azacytidine characterized by data selected from the group consisting of: a powder XRD pattern with peaks at about 5.8, 11.6, 12.8, 16.2, and 17.4±0.2 degrees two-theta; a PXRD pattern as depicted in FIG. 3; a single crystal XRD with the following data: monoclinic crystal system; unit cell parameters: a, b, c: a=5.14 Å, b=7.78 Å, c=15.40 Å, alpha=90°, beta=99.60°, and gamma=90°, respectively; an ORTEP view of a single crystal as depicted in FIG. 5; a solid-state $^{13}$C NMR spectrum having signals with chemical shifts at about 167.3, 156.2, and 93.4±0.2 ppm; a solid-state $^{13}$C NMR spectrum as depicted in FIG. 4; a solid-state $^{13}$C NMR spectrum having chemical shift differences between the signal exhibiting the lowest chemical shift and others in the chemical shift range of 90 to 180 ppm of about 62.8 and 73.9±0.1 ppm, and combinations thereof, containing less than about 20% by weight of crystalline 5-azacytidine having the most prominent 2 theta angles at 12.182, 13.024, 14.399, 16.470, 18.627, 19.049, 20.182, 21.329, 23.033, 23.872, 26.863, 27.1735, 29.277, 29.591, 30.369, and 32.072, designated "form I" or "crystalline form I". This form can be identified as "pure form VII" or "pure crystalline form VII". Preferably, pure crystalline 5-azacytidine form VII contains less than about 10%, more preferably, less than about 5%, most preferably less than about 1% by weight of crystalline 5-azacytidine form I. Preferably, the content of form I in pure form VII is measured by PXRD using the peak at about 20.2±0.2 degrees two-theta.

The signal exhibiting the lowest chemical shift in the chemical shift range of 90 to 180 ppm is typically at about 93.4±1 ppm.

The pure crystalline Form VII may be further characterized by a powder XRD pattern with peaks at about 20.8, 22.4, 25.9, 26.6, 29.2, 31.4, and 38.4±0.2 degrees two-theta. In addition, said crystalline form may be further characterized by a solid-state $^{13}$C NMR spectrum having signals with chemical shifts at about 84.5 and 75.3±0.2 ppm.

Furthermore, the pure crystalline Form VII may be further characterized by a solid-state $^{13}$C NMR spectrum having signals with chemical shifts at about 50.4 and 62.0±0.2 ppm.

Figure 6:
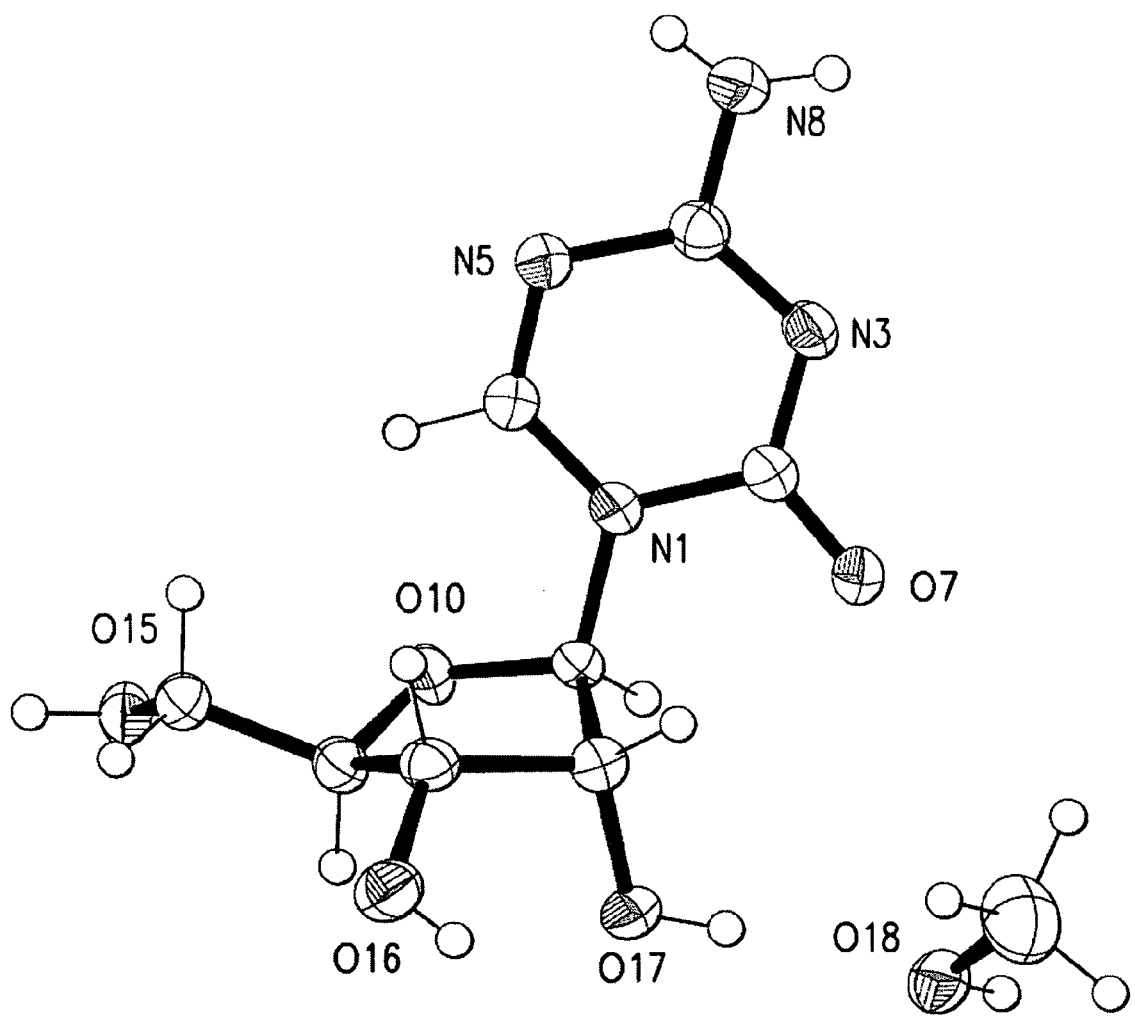
FIG. 6 illustrates the ORTEP view of a single crystal of pure crystalline 5-azacytidine Form VII.

The above pure crystalline Form VII is a solvated form of 5-azacytidine, preferably a methanol solvate, more preferably, a mono-methanol solvate. Preferably, the ratio of methanol to 5-azacytidine, as determined by solution $^1$H NMR analysis, is of about 1:1 (molecular ratio). The methanol solvate form may be also substantially identified by the spatial arrangement of 5-azacytidine and methanol molecules depicted in FIG. 6.

The pure crystalline form VII can be characterized by any other method known to a skilled artisan, such as, for example, FTIR and Raman spectroscopy.

The pure crystalline form VII crystallizes in well-developed crystals having an arrow-shaped morphology, and thus can be easily recovered by filtration. Preferably, the arrow-shaped crystals have a length of more than 10 μm. The advantage of having such crystal size is that the surface area is smaller and the crystalline material absorbs fewer impurities from the solution when it precipitates. Furthermore, the crystals of this crystalline 5-azacytidine are not as prone to electrostatic charging as the microcrystalline forms of 5-azacytidine that are present in prior-art, and thus can be easily manipulated without being scattered and lost, and without contamination of the working area. The environmental factor is especially important when working with substances such as 5-azacytidine.

The above pure crystalline form VII can be prepared by a process comprising crystallizing 5-azacytidine from a solvent mixture comprising methanol and a polar solvent selected from the group consisting of: a cyclic urea, a cyclic amide, and mixtures thereof.

A ratio of about 1 to about 50, preferably, about 1 to about 30 of methanol to the polar solvent by volume can be used.

The crystallization can comprise providing a solution of 5-azacytidine in a solvent mixture comprising methanol and a polar solvent selected from the group consisting of: cyclic urea, cyclic amide and mixtures thereof, and precipitating the said crystalline to obtain a suspension.

The crystallization can be performed by combining 5-azacytidine and the polar solvent; heating the combination to obtain a solution; cooling the solution; and admixing with methanol to facilitate the crystallization. Preferably, the heating is to a temperature of about 30° C. to about 130° C., more preferably, to a temperature 60° C. to about 90° C.

Preferably, the cyclic amide is a $C_{5-7}$ cyclic amide, and the cyclic urea is a $C_{3-6}$ cyclic urea. More preferably $C_{5-7}$ cyclic amides and the $C_{3-6}$ cyclic urea are selected from a group consisting of: N-methylpyrrolidone, 1,3-dimethyl-2-imidazolidinone, and 1,3-dimethyl-3,4,5,6-tetrahydro-2(1H)-pyrimidinone.

Preferably, the solution is cooled to a temperature of about 50° C. to about 0° C., more preferably to about 30° C. to about 20° C., prior to the addition of methanol.

Preferably, methanol is added to the solution.

After the addition of methanol, the obtained mixture is cooled to a temperature of about 20° C. to about –30° C., more preferably about 10° C. to about –10° C.

The process for preparing the above crystalline 5-azacytidine can further comprise a recovery process. The recovery can be performed by filtering the suspension, washing the filtered crystalline and drying it. Drying may be carried out at any suitable temperature, such as about 20° C. to about 50° C.

Figure 8:
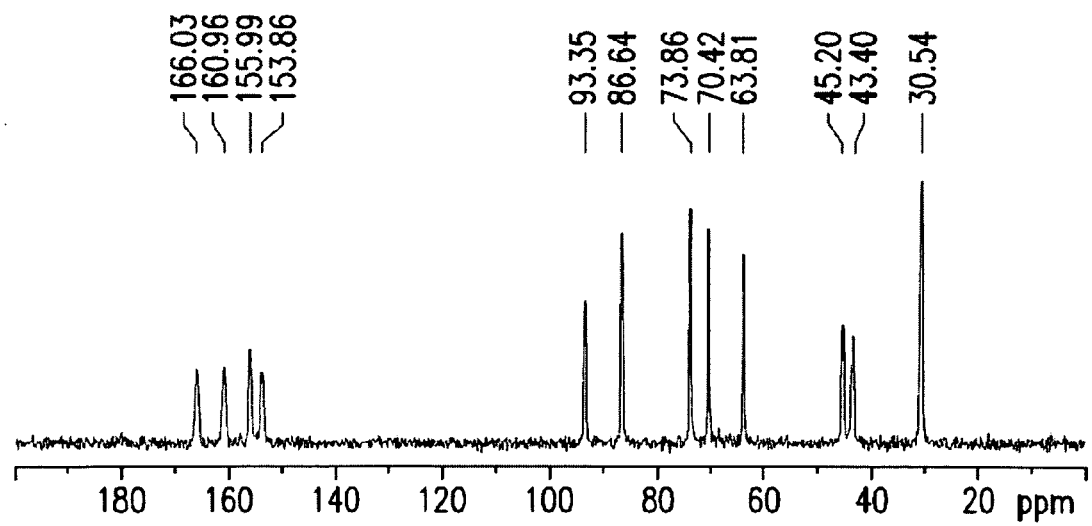
FIG. 8 illustrates a solid-state $^{13}$C NMR spectrum of the above crystalline 5-azacytidine Form XI.

The present invention provides a crystalline 5-azacytidine characterized by data selected from a group consisting of: a powder XRD pattern with peaks at about 8.5, 9.4, 12.0, 14.4, 17.1 and 31.3±0.2 degrees two-theta; a PXRD pattern as depicted in FIG. 7; a solid-state $^{13}C$ NMR spectrum having signals with chemical shifts at about 166.0, 153.9, and 93.4±0.2 ppm; a solid-state $^{13}C$ NMR spectrum as depicted in FIG. 8; a solid-state $^{13}C$ NMR spectrum having chemical shift differences between the signal exhibiting the lowest chemical shift and others in the chemical shift range of 90 to 180 ppm of about 60.5 and 72.6±0.1 ppm, and combinations thereof. The signal exhibiting the lowest chemical shift in the chemical shift range of 90 to 180 ppm is typically at about 93.4±1 ppm. This form can be designated Form XI.

The crystalline Form XI may be further characterized by a powder XRD pattern with peaks at about 19.3, 21.2, 25.8, and 28.6±0.2 degrees two-theta. Also, the said crystalline may be further characterized by a solid-state $^{13}C$ NMR spectrum having signals with chemical shifts at about 86.6 and 73.9±0.2 ppm.

Furthermore, the crystalline Form XI may be further characterized by a solid-state $^{13}C$ NMR having signals with chemical shifts at about 161.0, 43.3, and 30.5±0.2 ppm.

The above crystalline Form XI is a solvated form of 5-azacytidine, preferably a 1,3-dimethyl-2-imidazolidinone solvate, more preferably, a mono-1,3-dimethyl-2-imidazolidinone solvate. Preferably, the ratio of 1,3-dimethyl-2-imidazolidinone to 5-azacytidine, as determined by solution $^1H$ NMR analysis, is about 1:1 (molecular ratio).

The crystalline form can be characterized by any other method known to a skilled artisan, such as, for example, FTIR, and Raman spectroscopy.

The above crystalline Form XI has less than about 10%, preferably less than 5%, more preferably less than 1% by weight of 5-azacytidine forms I or III. The content of form I can be measured by PXRD using any one of the peaks at 12.2, 20.2 and 23.9 degrees two-theta. The content of form III can be measured by PXRD using any one of the peaks at 6.6, 17.4 and 22.7±0.2 degrees two-theta.

The above crystalline form XI of 5-azacytidine is prepared by a process comprising crystallizing 5-azacytidine from 1,3-dimethyl-2-imidazolidinone.

The crystallization is done by a process comprising providing a solution of 5-azacytidine in 1,3-dimethyl-2-imidazolidinone, and precipitating the said crystalline to obtain a suspension.

Preferably, the solution is provided by combining 5-azacytidine and 1,3-dimethyl-2-imidazolidinone and heating the combination. Preferably, the heating is to a temperature of about 50° C. to about 130° C., more preferably to about 60° C. to about 100° C., most preferably, to about 90° C.

Optionally, the solution of 5-azacytidine in 1,3-dimethyl-2-imidazolidinone can include a second solvent. The second solvent can be selected from, but not limited to a $C_3$-$C_8$ ketone such as methylethyketone, a $C_5$-$C_{12}$ aromatic or saturated hydrocarbon such as toluene, $C_2$-$C_8$ carboxylic acid ester such as ethylacetate, or $C_4$-$C_{10}$ ether such as t-butyl methyl ether Preferably, the precipitation is done by cooling the solution to a temperature of about 20° C. to about 0° C., more preferably to about 0° C. to about 10° C.

The process for preparing the above crystalline form XI of 5-azacytidine can further comprise a recovery process. The recovery may be performed by filtering the suspension, washing the filtered crystalline and drying it. Drying may be carried out at any suitable temperature, such as about 20° C. to about 50° C.

Figure 9:
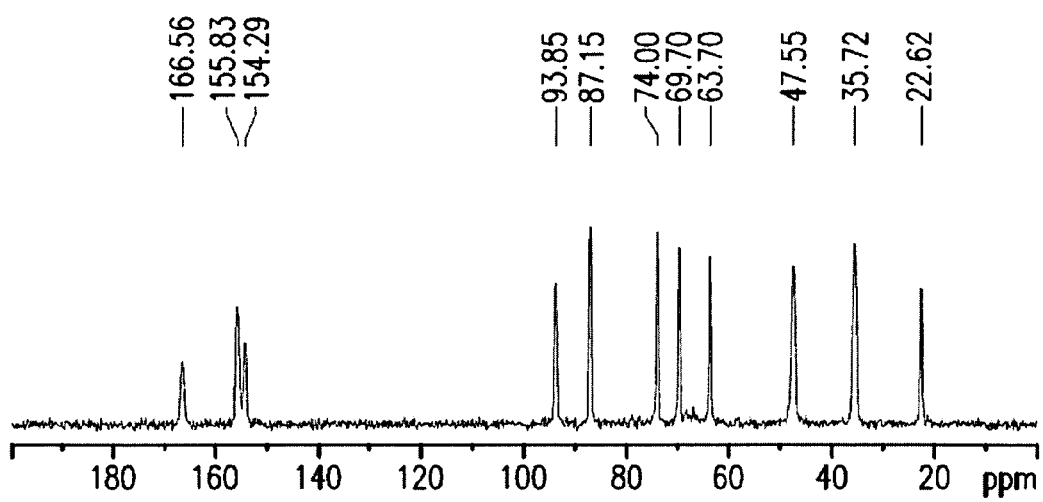
FIG. 9 illustrates a powder X-ray diffraction pattern of crystalline 5-azacytidine Form XII.
Figure 10:
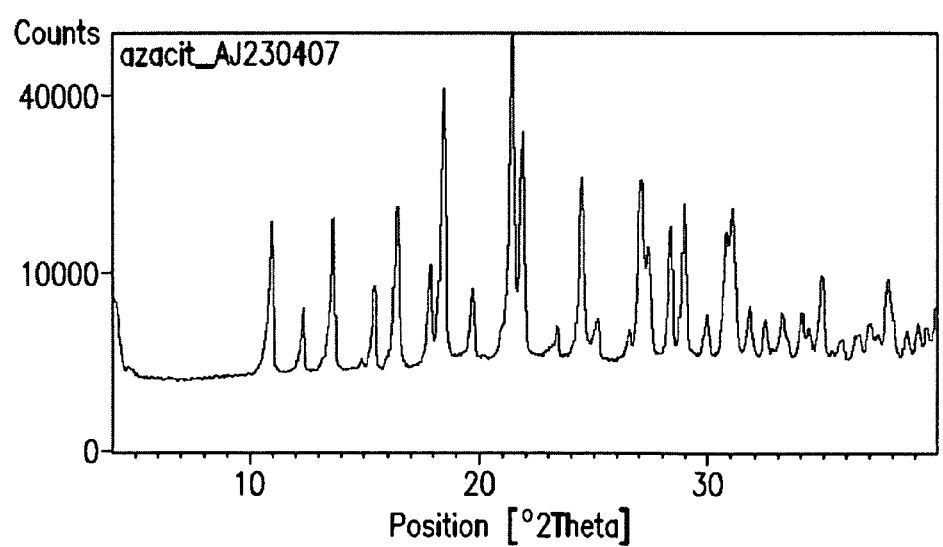
FIG. 10 illustrates a solid-state $^{13}$C NMR spectrum of crystalline 5-azacytidine Form XII.

The present invention provides crystalline 5-azacytidine characterized data selected from a group consisting of: a powder XRD pattern with peaks at about 9.4, 11.8, 12.1, 14.3 and 16.5±0.2 degrees two-theta; a PXRD pattern as depicted in FIG. 9; a solid-state $^{13}C$ NMR spectrum having signals with chemical shifts at about 166.6, 154.3, and 93.9±0.2 ppm; a solid-state $^{13}C$ NMR spectrum having signals with chemical shifts at about 166.6, 155.8, and 93.9±0.2 ppm; a solid-state $^{13}C$ NMR spectrum as depicted in FIG. 10; a solid-state $^{13}C$ NMR spectrum having chemical shift differences between the signal exhibiting the lowest chemical shift and another in the chemical shift range of 90 to 180 ppm of about 60.4 and 72.7±0.1 ppm, a solid-state $^{13}C$ NMR spectrum having chemical shift differences between the signal exhibiting the lowest chemical shift and others in the chemical shift range of 90 to 180 ppm of about 61.9 and 72.7±0.1 ppm, and combinations thereof. The signal exhibiting the lowest chemical shift in the chemical shift range of 90 to 180 ppm is typically at about 93.9±1 ppm. This form can be designated form XII.

The crystalline Form XII may be further characterized by a powder XRD pattern with peaks at about 18.9, 20.5, 21.1, 26.0, and 28.6±0.2 degrees two-theta. In addition, the said crystalline may be further characterized by a solid-state $^{13}$C NMR spectrum having chemical shifts at about 87.2 and 74.0±0.2 ppm.

Furthermore, the crystalline form XII may be further characterized by a solid-state $^{13}$C NMR spectrum having signals with chemical shifts at about 22.6, 35.7, and 47.6±0.2 ppm.

The above crystalline form XII is a solvated form of 5-azacytidine, preferably a 1,3-dimethyl-3,4,5,6-tetrahydro-2 (1H)-pyrimidinone solvate, more preferably, a mono-1,3-dimethyl-3,4,5,6-tetrahydro-2(1H)-pyrimidinone solvate. Preferably, the molecular ratio of 1,3-dimethyl-3,4,5,6-tetrahydro-2(1H)-pyrimidinone to 5-azacytidine, as determined by solution $^{1}$H NMR analysis, is about 1:1.

The crystalline form XII can be characterized by any other method known to a skilled artisan, such as, for example, FTIR, and Raman spectroscopy.

The above crystalline Form XII has less than about 10%, preferably less than 5%, and more preferably less than 1% by weight of 5-azacytidine form III. The content of form III can be measured by PXRD using any of the peaks at 6.6, 15.1 and 22.3±0.2 degrees two-theta.

The above crystalline form XII of 5-azacytidine is prepared by a process comprising crystallizing 5-azacytidine from 1,3-dimethyl-3,4,5,6-tetrahydro-2(1H)-pyrimidinone.

The crystallization is done by a process comprising providing a solution of 5-azacytidine in 1,3-dimethyl-3,4,5,6-tetrahydro-2(1H)-pyrimidinone, and precipitating the said crystalline to obtain a suspension.

Preferably, the solution is provided by combining 5-azacytidine and 1,3-dimethyl-3,4,5,6-tetrahydro-2(1H)-pyrimidinone and heating the combination. Preferably, the heating is to a temperature of about 50° C. to about 130° C., more preferably to about 60° C. to about 100° C., most preferably, to about 90° C.

Optionally, the solution of 5-azacytidine in 1,3-dimethyl-3,4,5,6-tetrahydro-2(1H)-pyrimidinone can include a second solvent. The second solvent can be selected from, but not limited to a $C_3$-$C_8$ ketone such as methylethylketone ("MEK", 2-butanone), a $C_5$-$C_{12}$ aromatic or saturated hydrocarbon such as toluene, a $C_2$-$C_8$ carboxylic acid ester such as ethylacetate, or a $C_4$-$C_{10}$ ether such as t-butyl methyl ether.

Preferably, the precipitation is done by cooling the solution to a temperature of about 20° C. to about –30° C., more preferably to about 0° C. to about 10° C.

The process for preparing the above crystalline form XII of 5-azacytidine can further comprise a recovery process. The recovery may be performed by filtering the suspension, washing the filtered crystalline and drying it. Drying may be carried out at any suitable temperature, such as about 20° C. to about 50° C.

The PXRD diffractogram of form V disclosed in FIG. 5 of U.S. Pat. No. 7,078,518 shows the presence of peaks of form I at approximately 13.176, 14.548, 19.202 and 20.329 degrees two-theta. Thus, the disclosed form V is a mixture of form V and about 30% by weight of form I. The content of form I can be measured by PXRD using any one of the peaks at 13.2, 14.5, 20.2, 23.0 and 23.8±0.2 degrees two-theta.

The present invention provides crystalline 5-azacytidine characterized by data selected from the group consisting of: a powder XRD pattern with peaks at about 11.0, 12.4, 13.7, 16.5, and 18.5±0.2 degrees two-theta; a PXRD pattern as depicted in FIG. 11, and a combination thereof, containing less than about 20% by weight of crystalline 5-azacytidine form I. This form can be identified as "pure form V" or "pure crystalline form V". Preferably, pure crystalline 5-azacytidine form V contains less than about 10%, more preferably less than about 5%, and most preferably less than about 1% by weight of crystalline 5-azacytidine form I. Preferably, the content of form I in the pure form V is measured by PXRD using any one of the peaks at about 13.2, 14.5, 20.2, 23.0 and 23.8±0.2 degrees two-theta.

The pure crystalline form V may be further characterized by a powder XRD pattern with peaks at about 15.5, 24.5, 27.1, 28.4, and 29.0±0.2 degrees two-theta.

The pure crystalline form V can be characterized by any other method known to a skilled artisan, such as, for example, FTIR, and Raman spectroscopy.

The above pure crystalline form V of 5-azacytidine is prepared by a process comprising lyophilizing a solution of 5-azacytidine in dimethylsulfoxide. Lyophilization is also known as freeze-drying.

In the lyophilization process, a solution of 5-azacytidine in dimethylsulfoxide is frozen, and then the frozen mass is subjected to a pressure of less than one atmosphere, to remove the solvent.

Preferably, the solution is provided by a process comprising combining 5-azacytidine and dimethylsulfoxide and heating the combination. Preferably, the heating is to a temperature of about 50° C. to about 130° C., more preferably at about 70° C. to about 80° C.

Preferably, freezing the solution is done gradually. First, cooling to a temperature of about 30° C. is done, and then cooling to a temperature of about 18° C. to about –30° C., is performed, providing a frozen solution. Typically, the evaporation of the solvents is done at about 18° C. to about –30° C. Preferably, evaporation of the solvent is done under reduced pressure (less than one atmosphere). Preferably, the reduced pressure is used in the range of about 0.01 to 100 mBar, more preferably at about 0.1 to about 3 mBar.

5-azacytidine used as a starting material in the above processes of the present invention (including processes that proceed through a solution or slurry) may be prepared according to known to a skilled artisan, including those disclosed in U.S. Pat. Nos. 6,887,885, 6,943,249, 7,078,518, which are incorporated herein by reference. Preferably, the starting 5-azacytidine in the process for preparing 5-azacytidine containing about 10 ppm to about 2000 ppm of non-volatile solvents; wherein the obtained 5-azacytidine is also pure crystalline 5-azacytidine form I, can be selected from a group consisting of: crude 5-azacytidine, crystalline 5-azacytidine having the most prominent 2 theta angles at 5.704, 11.571, 12.563, 14.070, 15.943, 16.993, 18.066, 20.377, 20.729, 21.484, 21.803, 22.452, 22.709, 23.646, 24.068, 25.346, 25.346, 26.900, 27.991, 28.527, 28.723, 30.124, 30.673, 31.059, 35.059, 38.195 and 38.403, designated form IV, crystalline 5-azacytidine form IX, crystalline 5-azacytidine form VII, and crystalline 5-azacytidine form III. Crude 5-azacytidine can be 5-azacytidine anhydrate, hydrate, solvate or mixtures thereof. Preferably, crude 5-azacytidine is a mixture of forms I and II.

The crystalline forms of the present invention can be used to prepare formulations for treating myelodysplactic syndromes.

The present invention encompasses a pharmaceutical composition comprising any one of the above forms of 5-azacytidine, and at least one pharmaceutically acceptable excipient; wherein the 5-azacytidine includes also 5-azacytidine containing about 10 ppm to about 2000 ppm of non-volatile solvents.

The present invention also encompasses a pharmaceutical composition comprising anyone of the above forms of 5-azacytidine prepared according to the processes of the present invention, and at least one pharmaceutically acceptable excipient; wherein the 5-azacytidine includes also 5-azacytidine containing about 10 ppm to about 2000 ppm of non-volatile solvents.

The present invention further encompasses a process for preparing a pharmaceutical formulation comprising combining anyone of the above forms of 5-azacytidine with at least one pharmaceutically acceptable excipient; wherein the 5-azacytidine includes also 5-azacytidine containing about 10 ppm to about 2000 ppm of non-volatile solvents.

The present invention encompasses a process for preparing a pharmaceutical composition comprising anyone of the above forms of 5-azacytidine, prepared according to the processes of the present invention, and at least one pharmaceutically acceptable excipient; wherein the 5-azacytidine includes also 5-azacytidine containing about 10 ppm to about 2000 ppm of non-volatile solvents.

The present invention further encompasses the use of any one of the above forms of 5-azacytidine, for the manufacture of a pharmaceutical composition; wherein the starting 5-azacytidine includes also 5-azacytidine containing about 10 ppm to about 2000 ppm of non-volatile solvents.

The present invention further encompasses the use of any one of the 5-azacytidine crystals forms provided by the invention, for the manufacture of a pharmaceutical composition.

Methods of administration of a pharmaceutical composition of the present invention may comprise administration in various preparations depending on the age, sex, and symptoms of the patient. The pharmaceutical compositions can be administered, for example, as tablets, pills, powders, suspensions, emulsions, granules, capsules, suppositories, injection preparations, and the like. When the pharmaceutical composition is a liquid pharmaceutical composition, it will be in the form of a suspension or emulsion wherein the 5-deazacytidine retains its crystalline form.

Pharmaceutical compositions of the present invention can optionally be mixed with other forms of 5-deazacytidine and/or other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like.

Diluents increase the bulk of a solid pharmaceutical composition and can make a pharmaceutical dosage form containing the composition easier for the patient and care giver to handle. Diluents for solid compositions include, for example, microcrystalline cellulose (e.g., Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, or talc.

Carriers for use in the pharmaceutical compositions may include, but are not limited to, lactose, white sugar, sodium chloride, glucose, urea, starch, calcium carbonate, kaolin, crystalline cellulose, or silicic acid.

Binders help bind the active ingredient and other excipients together after compression. Binders for solid pharmaceutical compositions include for example acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, or starch.

Disintegrants can increase dissolution. Disintegrants include, for example, alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Disintegration inhibitors may include, but are not limited to, white sugar, stearin, coconut butter, hydrogenated oils, and the like.

Absorption accelerators may include, but are not limited to, quaternary ammonium base, sodium laurylsulfate, and the like.

Wetting agents may include, but are not limited to, glycerin, starch, and the like. Adsorbing agents may include, but are not limited to, starch, lactose, kaolin, bentonite, colloidal silicic acid, and the like.

A lubricant can be added to the composition to reduce adhesion and ease release of the product from a punch or dye during tableting. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Glidants can be added to improve the flowability of non-compacted solid composition and improve the accuracy of dosing. Excipients that can function as glidants include for example colloidal silicon dioxide, magnesium trisilicate, powdered cellulose, starch, talc and tribasic calcium phosphate.

Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid.

Tablets can be further coated with commonly known coating materials such as sugar coated tablets, gelatin film coated tablets, tablets coated with enteric coatings, tablets coated with films, double layered tablets, and multi-layered tablets. Capsules can be coated with shell made, for example, from gelatin and optionally contain a plasticizer such as glycerin and sorbitol, and an opacifying agent or colorant.

Solid and liquid compositions can also be dyed using any pharmaceutically acceptable colorant to improve their appearance and/or facilitate patient identification of the product and unit dosage level.

In liquid pharmaceutical compositions of the present invention, the 5-deazacytidine is suspended or otherwise dispersed in a liquid carrier, retaining its crystalline form. A dispersant, such as for example sodium lauryl sulfate, may optionally be employed to stabilize the preparation; suitable dispersants are known to those skilled in the art. Suitable liquid carriers include, but are not limited to, water, vegetable oils, alcohol, polyethylene glycol, propylene glycol and glycerin, and combinations thereof. Other solid ingredients, which may optionally be present, can be dissolved or suspended in the carrier.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain viscosity enhancing agents to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at safe levels to improve storage stability.

A liquid pharmaceutical composition according to the present invention can also contain a buffer, such as for example gluconic acid, lactic acid, citric acid, acetic acid, phosphoric acid, and pharmaceutically acceptable salts thereof.

Selection of excipients and the amounts to use can be readily determined by an experienced formulation scientist in view of standard procedures and reference works known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can also be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like.

For the purpose of shaping the pharmaceutical composition in the form of suppositories, any commonly known excipient used in the art can be used. For example, excipients include, but are not limited to, polyethylene glycols, coconut butter, higher alcohols, esters of higher alcohols, gelatin, semisynthesized glycerides, and the like.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added.

The amount of a 5-azacytidine crystal form of the present invention contained in a pharmaceutical composition is not specifically restricted, and an effective dose may be divided among two or more individual dose units (e.g., tablets or capsules). In general, the total dose should be sufficient to treat, ameliorate, or reduce the myelodysplastic syndrome for which treatment is intended.

Having described the invention with reference to certain preferred embodiments, other embodiments will become apparent to one skilled in the art from consideration of the specification. The invention is further defined by reference to the following examples describing in detail the process and compositions of the invention. It will be apparent to those skilled in the art that many modifications, both to materials and methods, may be practiced without departing from the scope of the invention.

EXAMPLES

Instruments

PXRD

XRD diffraction was performed on X-Ray powder diffractometer: Philips X'pert Pro powder diffractometer, CuK$_\alpha$ radiation, $\lambda$=1.5418 Å. X'Celerator detector active length (2 theta)=2.122°, laboratory temperature 22-25° C.

Single Crystal XRD Method

Data were collected on Xcalibur PX, Cu K$\alpha$ using combined $\phi$ and $\omega$ scans. All non-hydrogen atoms were refined anisotropically, hydrogen atoms were refined riding in expected geometric positions, OH hydrogen atoms were located from fourier maps. Data collection: *CrysAlis RED* (Oxford Diffraction, 2002); cell refinement: *CrysAlis RED*; data reduction: *CrysAlis RED*; program used to solve structure: SIR92 (Altomare et al., 1994); program used to refine structure: *CRYSTALS* (Betteridge et al., 2003)

DSC

DSC measurements were performed on Differential Scanning Calorimeter DSC823e (Mettler Toledo). Al crucibles 40 μl with PIN were used for sample preparation. Usual weight of sample was 1-2.5 mg. Program: temperature range was 50° C.-300° C., 10° C./min.

NMR Spectroscopy in Solution

NMR spectra of solutions in deuterated dimethylsulfoxide were obtained at 30° C. on a Varian INOVA-400 spectrometer, at 399.87 MHz for $^1$H and 100.55 MHz for $^{13}$C.

Solid-State $^{13}$C NMR

The CP/MAS$^{13}$C NMR measurements were made on a Bruker Avance 500 NMR US/WB spectrometer in a 4-mm ZrO$_2$ rotor. Magic angle spinning (MAS) speed was 10 kHz. As used herein, the term "$^{13}$C NMR chemical shifts" refers to the shifts measured under above-specified conditions, however, these shifts can slightly differ from instrument to instrument, and can be shifted either upfield or downfield due to the particular instrumental setup and calibration used. Nevertheless the sequence of individual peaks remains identical.

GC

Residual solvents were determined by gas chromatography using head-space sampling. Headspace instrument HP7694 together with Gas chromatograph A6890 equipped with FID detector (Agilent technologies).

Example 1

Preparation of Crystalline Form IX of 5-Azacytidine

5-Azacytidine (500 mg) was dissolved in N-methylpyrrolidone (5 ml) at 90° C. Then, the solution was allowed to crystallize at 15° C. without stirring for overnight. The white solid was filtered, washed subsequently with toluene (20 ml) and n-hexane (20 ml) and dried in a stream of nitrogen for 1 h to obtain the crystalline form. (594 mg).

Example 2

Preparation of Pure Crystalline Form VII of 5-Azacytidine 5-azacytidine (1 g, 97.3% by HPLC) was dissolved in N-methylpyrrolidone (5 ml) at 115° C. Solution was allowed to cool to 40° C. and methanol was added with stirring (90 ml). The solution was allowed to crystallise overnight at 20° C. in a form of large, arrow-shaped crystals having length above 10 µm. The crystalline form was recovered by filtration, washed with diethyl ether (20 ml), n-hexane (10 ml), and dried under a stream of nitrogen at 25° C. (807 mg, 98.5% by HPLC).

Example 3

Preparation of Pure Crystalline Form VII of 5-Azacytidine 5-azacytidine (1 g, 97.3% by HPLC) was dissolved in 1,3-dimethyl-2-imidazolidinone (9 ml) at 90° C. Solution was allowed to cool to 40° C. and methanol was added with stirring (90 ml). The solution was allowed to crystallize overnight at 20° C. in a form large, arrow-shaped crystals having length above 10 µm. the crystalline form was recovered by filtration, washed with diethyl ether (20 ml), n-hexane (10 ml), and dried in a stream of nitrogen at 25° C. (930 mg, 98.1% by HPLC).

Example 4

Preparation of Pure Crystalline Form VII of 5-Azacytidine 5-azacytidine (1 g, 97.3% by HPLC) was dissolved in 1,3-dimethyl-3,4,5,6-tetrahydro-2(1H)-pyrimidinone (5 ml) at 115° C. Solution was allowed to cool to 40° C. and methanol was added with stirring (90 ml). The solution was allowed to crystallize overnight at 20° C. in a form large, arrow-shaped crystals having length above 10 µm. The crystalline form was recovered by filtration, washed with diethyl ether (20 ml), n-hexane (10 ml), and dried in a stream of nitrogen at 25° C. (960 mg, 99.0% by HPLC).

Example 5

Preparation of Crystalline Form XI of 5-Azacytidine

5-Azacytidine (900 mg) was dissolved in 1,3-dimethyl-2-imidazolidinone (9 ml) at 90° C. Then the solution was allowed to crystallize at 15° C., without stirring for overnight The white solid was filtered, washed subsequently with diethyl ether (50 ml) and n-hexane (50 ml) and dried in a stream of nitrogen for 1 h to obtain the crystalline form. (1146 mg).

Example 6

Preparation of Crystalline Form XII of 5-Azacytidine

5-Azacytidine (900 mg) was dissolved in 1,3-dimethyl-3,4,5,6-tetrahydro-2(1H)-pyrimidinone (5 ml) at 90° C. and 2-butanone (10 ml) was added to the solution. Then the solution was allowed to crystallize without stirring at −30° C. overnight. The white solid was filtered, washed subsequently with diethyl ether (50 ml) and n-hexane (50 ml) and dried in a stream of nitrogen for 1 h to obtain the crystalline form. (990 mg).

Example 7

Preparation of Pure Crystalline Form V of 5-Azacytidine

5-Azacytidine (350 mg) was dissolved in dimethylsulfoxide (7 ml) at 80° C. Then the solution was allowed to cool to 30° C. and put to the refrigerator set at −30° C. The frozen liquid was put the lyophiliser and dimethylsulfoxide was evaporated within 24 h at 1.5 mBar and 15° C.

Example 8

Preparation of Pure Crystalline Form I of 5-Azacytidine from a Mixture of Crystalline Form I and Crystalline 5-Azacytidine Form II in N-Butanol Crude 5-azacytidine (1 g) containing about 80% of form II and 20% of form I, was suspended in n-butanol (50 ml). The suspension was heated to 117° C. for 15 min. the suspension was allowed to cool to 25° C. and 5-azacytidine form I was recovered by filtration, washed with acetone (10 ml), petrolether (10 ml), and dried in a stream of nitrogen at 25° C. (0.83 g, yield: 83%).

Example 9

Preparation of Pure Crystalline Form I of 5-Azacytidine from a Mixture of Crystalline Form I and Crystalline 5-Azacytidine Form II in Ethanol Crude 5-azacytidine (1 g) containing about 80% of form II and 20% of form I was suspended in ethanol (50 ml). The suspension was heated to 78° C. for 15 min. The suspension was allowed to cool to 25° C. and 5-azacytidine form I was recovered by filtration, washed with acetone (10 ml), petro-lether (10 ml), and dried in a stream of nitrogen at 25° C. (0.82 g, yield: 82%).

Example 10

Preparation of Pure Crystalline Form I of 5-Azacytidine from a Mixture of Crystalline Form I and Crystalline 5-Azacytidine Form II in 1,4-Dioxane Crude 5-azacytidine (1 g) containing about 80% of form II and 20% of form I was suspended in 1,4-dioxane (50 ml). The suspension was heated to 101° C. for 15 min. The suspension was allowed to cool to 25° C. and 5-azacytidine form I was recovered by filtration, washed with acetone (10 ml), petro-lether (10 ml), and dried in a stream of nitrogen at 25° C. (0.83 g, yield: 83%).

Example 11

Preparation of Pure Crystalline Form I of 5-Azacytidine from Crystalline Form IX of 5-Azacytidine Crystalline form of IX of 5-azacytidine (500 mg) was suspended in n-butanol (20 ml). The suspension was heated to 117° C. for 15 min. The suspension was allowed to cool to 25° C. and 5-azacytidine form I was recovered by filtration, washed with diethyl ether (20 ml), and n-hexane (20 ml), and dried in a stream of nitrogen at 25° C. (277 mg, yield: 78%).

Example 12

Preparation of Pure Crystalline Form I of 5-Azacytidine from Pure Crystalline Form VII of 5-Azacytidine Crystalline form of VII 5-azacytidine (400 mg) was suspended in n-butanol (15 ml). The suspension was heated to 117° C. for 15 min. The suspension was allowed to cool to 25° C. and 5-azacytidine form I was recovered by filtration, washed with diethyl ether (20 ml), and n-hexane (20 ml), and dried in a stream of nitrogen at 25° C. (223 mg, yield: 82%).

Example 13

Preparation of Pure Crystalline Form I of 5-Azacytidine from Crystalline 5-Azacytidine Form III in Ethanol 5-Azacytidine (1 g) form III was suspended in ethanol (20 ml). The suspension was heated to 78° C. for 15 min. The suspension was allowed to cool to 25° C. and azacytidine form I was recovered by filtration, washed with acetone (15 ml), and n-hexane (20 ml), and dried in a stream of nitrogen at 25° C. (856 mg, yield: 92%).

Comparative Example 14

Crystallization of 5-Azacytidine According to US '855 Example 1

5-Azacytidine (1.14 g) was dissolved in dimethylsulfoxide (25 ml) by heating to 90° C. for 10 min. The solution was cooled to about 40° C. and methanol (250 ml) was added with stirring. The solution was placed into refrigerator set at −20° C. for 24 hours. The crystalline material was recovered by filtration, washed with methanol (50 ml) and dried at 35° C., 1 mBar for 2 h (1.07 g). The measurement of powder diffraction pattern revealed that the solid is a mixture of 5-azacytidine form I and form VII containing about 40% of form I. The mixture was further characterized by the content of residual solvents as measured by GC: methanol 62 370 ppm and DMSO 5570 ppm.

Example 15

Preparation of Pure Crystalline Form I Having Low Residual Solvents

5-Azacytidine (350 mg) prepared according to Example 14 was suspended in n-butanol (10 ml). The suspension was heated to 117° C. for 15 min. The suspension was allowed to cool to 25° C. and 5-azacytidine was recovered by filtration, washed with n-butanol (10 ml) and dried at 35° C., 1 mBar for 2 h (305 mg). The measurement of powder diffraction pattern revealed that the solid is pure 5-azacytidine form I. 5-Azacytidine form I was further characterized by the content of residual solvents as measured by GC: methanol 244 ppm, DMSO 262 ppm, and n-butanol 1161 ppm.

Example 16

Preparation of Pure Crystalline Form I Having Low Residual Solvents

5-Azacytidine (350 mg) prepared according to Example 14 was suspended in iso-amyl alcohol (10 ml). The suspension was heated to 131° C. for 15 min. The suspension was allowed to cool to 25° C. and 5-azacytidine was recovered by filtration, washed with iso-amyl alcohol (10 ml) and dried at 35° C., 1 mBar for 2 h (310 mg). The measurement of powder diffraction pattern revealed that the solid is pure 5-azacytidine form I. 5-Azacytidine form I was further characterized by the content of residual solvents as measured by GC: methanol 213 ppm, DMSO 197 ppm, and iso-amyl alcohol 1519 ppm.

Example 17

Preparation of Crystalline Form IX of 5-Azacytidine

5-Azacytidine (1.25 g) was dissolved in N-methylpyrroli-done (12.5 ml) at 120° C., cooled to 25° C. and 2-butanone (90 ml) was added with stirring and the mixture was allowed to stand 3 h at 20° C. 5-Azacytidine form IX was recovered by filtration, washed with 2-butanone (10 ml), petroleum ether (10 ml), and dried in air (1.48 g).

Example 18

Preparation of Crystalline Form XII of 5-Azacytidine

5-Azacytidine (900 mg) was dissolved in 1,3-dimethyl-3,4,5,6-tetrahydro-2(1H)-pyrimidinone (6 ml) at 90° C., cooled to 25° C. and t-butyl methyl ether (10 ml) was added to the solution. Then the solution was allowed to crystallize without stirring at −30° C. overnight. The white solid was filtered, washed subsequently with diethyl ether (50 ml) and n-hexane (50 ml) and dried in a stream of nitrogen for 1 h to obtain the 5-azacytidine form XII. (990 mg).

Example 19

Preparation of Pure Crystalline Form I of 5-Azacytidine from Crystalline Form IV in Ethanol 5-Azacytidine form IV (1 g), was suspended in ethanol (25 ml). The suspension was heated to 78° C. for 15 min. the suspension was allowed to cool to 25° C. and 5-azacytidine form I was recovered by filtration, washed with acetone (10 ml), hexane (10 ml), and dried in a stream of nitrogen at 25° C. (0.76 g, yield: 76%).

Example 20

Preparation of Pure Crystalline Form I of 5-Azacytidine from a Mixture of Crystalline Form I and Crystalline 5-Azacytidine Form II in Pyridine 5-Azacytidine (1 g) containing about 80% of form II and 20% of form I, was suspended in pyridine (50 ml). The suspension was heated to 115° C. for 15 min. the suspension was allowed to cool to 25° C. and 5-azacytidine form I was recovered by filtration, washed with acetone (10 ml), petro-lether (10 ml), and dried in a stream of nitrogen at 25° C. (0.59 g, yield: 59%).

What is claimed is:

1. 5-Azacytidine containing about 10 ppm to about 2000 ppm of non-volatile solvents.

2. The 5-azacytidine of claim 1 containing about 10 ppm to about 500 ppm of non-volatile solvents.

Figure 13:
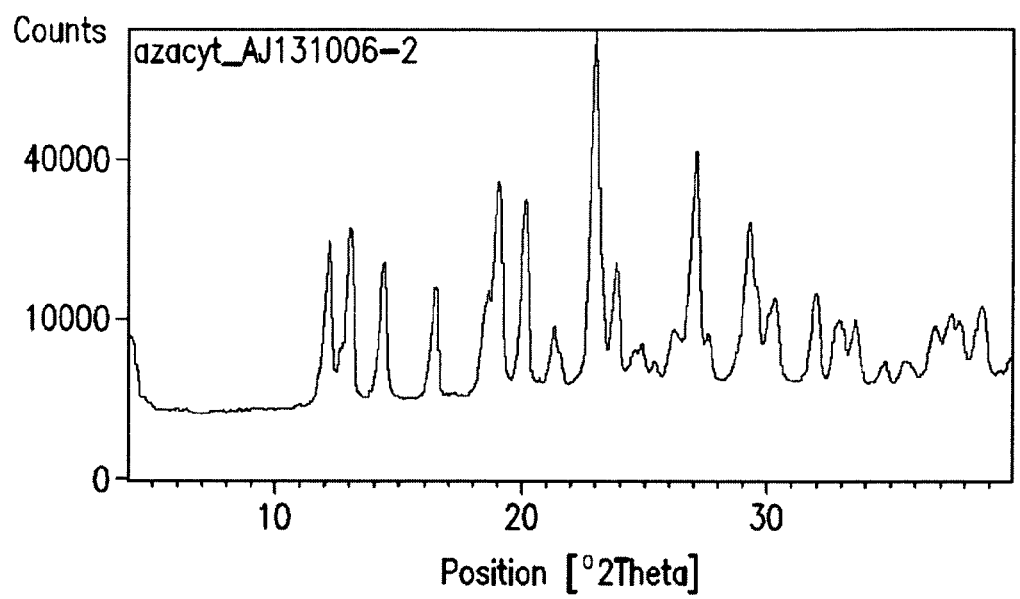
FIG. 13 illustrates a powder X-ray diffraction pattern for pure crystalline 5-azacytidine form I

3. The 5-azacytidine of claim 1, wherein said 5-azacytidine is crystalline 5-azacytidine characterized by data selected from the group consisting of: a PXRD pattern with peaks at about 12.2, 13.1, 14.4, 16.2, and 23.1±0.2 degrees two-theta, a PXRD pattern as depicted in FIG. 13, and a combination thereof, said crystalline 5-azacytidine containing less than about 5% by weight of a crystalline 5-azacytidine having most prominent diffractions at PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta, and less than about 5% by weight of a crystalline 5-azacytidine having most prominent PXRD diffractions at 13.4, 17.6, and 22.1 degrees two-theta.

4. A method for preparing the 5-azacytidine of claim 1 comprising heating a suspension of 5-azacytidine in a single polar organic solvent selected from the group consisting of: an aliphatic alcohol, a nitrile, an ether, nitromethane, pyridine, or in a mixture of solvents comprising said polar organic solvent and a non-polar organic solvent selected from the group consisting of: a ketone, a hydrocarbon, or an ester, and recovering 5-azacytidine containing about 10 ppm to about 2000 ppm of non-volatile solvents; wherein the single polar solvent or its mixture with a non-polar solvent has boiling point of less than 140° C.

5. The method of claim 4, wherein the obtained 5-azacytidine is crystalline 5-azacytidine characterized by data selected from the group consisting of: a PXRD pattern with peaks at about 12.2, 13.1, 14.4, 16.2, and 23.1±0.2 degrees two-theta, a PXRD pattern as depicted in FIG. 13, and a combination thereof containing less than about 5% by weight of a crystalline 5-azacytidine having most prominent diffractions at PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta, and less than about 5% by weight of a crystalline 5-azacytidine having most prominent PXRD diffractions at 13.4, 17.6, and 22.1 degrees two-theta.

6. The method of claim 4, wherein the starting 5-azacytidine is selected from the group consisting of: crude 5-azacytidine, crystalline 5-azacytidine having the most prominent PXRD diffractions at 2theta angles at 5.704, 11.571, 12.563, 14.070, 15.943, 16.993, 18.066, 20.377, 20.729, 21.484, 21.803, 22.452, 22.709, 23.646, 24.068, 25.346, 25.346, 26.900, 27.991, 28.527, 28.723, 30.124, 30.673, 31.059, 35.059, 38.195 and 38.403, crystalline 5-azacytidine characterized by data selected from the group consisting of: a PXRD pattern with peaks at about 8.7, 9.5, 12.1, 14.4 and 17.3±0.2 degrees two-theta; a PXRD pattern as depicted in FIG. 1; a solid-state $^{13}$C NMR spectrum having signals with chemical shifts at about 166.2, 155.9, and 154.2±0.2 ppm; a solid-state $^{13}$C NMR spectrum as depicted in FIG. 2; a solid-state $^{13}$C NMR spectrum having chemical shift differences between the signal exhibiting the lowest chemical shift and another in the chemical shift range of 90 to 180 ppm of about 60.5, 62.2, and 72.5±0.1 ppm, and a combination thereof, crystalline 5-azacytidine which exhibits distinctive PXRD peaks at 5.8, 11.5, 12.8, 22.4, and 26.6 degrees two-theta, and crystalline 5-azacytidine having most prominent diffractions on PXRD at two theta values at 6.566, 11.983, 13.089, 15.138, 17.446, 20.762, 21.049, 22.776, 24.363, 25.743, 26.305, 28.741, 31.393, 32.806, 33.043, 33.536, 36.371, 39.157, and 41.643 degrees two-theta.

7. The method of claim 4, wherein the suspension of 5-azacytidine is provided by combining 5-azacytidine and a single polar organic solvent or with a mixture of solvents comprising said single polar organic solvent and a non-polar organic solvent.

8. The method of claim 7, wherein the aliphatic alcohol is a $C_{2-6}$ aliphatic alcohol, the nitrile is $C_{2-4}$ nitrile, and the ether is a $C_{3-8}$ ether including penta or hexa-cyclic ether.

9. The method of claim 8, wherein the $C_{2-6}$ aliphatic alcohol is methanol, ethanol, 2-propanol, 1-propanol, 1-butanol, 2-butanol, i-butanol, amylalcohol, methoxyethanol, ethoxyethanol or mixtures thereof, the $C_{2-4}$ nitrile is acetonitrile, and the $C_{3-8}$ ether including penta or hexa-cyclic ether is dimethoxyethane, tert-butylmethylether, dioxolane, tetrahydrofuran, methyl-tetrahydrofuran, or dioxane.

10. The method of claim 9, wherein the $C_{2-6}$ aliphatic alcohol is 1-butanol or ethanol.

11. The method of claim 9, wherein the $C_{3-8}$ ether including penta or hexa-cyclic ether is 1,4-dioxane.

12. The method of claim 4, wherein the ketone is a $C_{3-6}$ ketone, the ester is a $C_{2-6}$ ester, and the hydrocarbon is a $C_{6-10}$ hydrocarbon.

13. The method of claim 12, wherein the $C_{3-6}$ ketone is acetone, methyl-ethylketone, or methylbutylketone, the $C_{2-6}$ ester is ethylacetate, propyl acetate, isopropyl acetate, butylacetate, or isobutylacetate, and the $C_{6-10}$ hydrocarbon is hexane, heptane, cyclo-hexane, methylcyclohexane, toluene, m-xylene, p-xylene, or chlorobenzene.

14. The method of claim 13, wherein the $C_{3-6}$ ketone is methylethyl ketone or methylisobutyl ketone, the $C_{2-6}$ ester is ethylacetate, and the $C_{6-10}$ hydrocarbon is toluene.

15. The method of claim 4, wherein the solvent used to prepare the suspension is a single polar organic solvent, selected from ethanol and 1-butanol.

16. The method of claim 4, wherein the suspension is heated to a temperature of about 30° C. to about 130° C.

17. Crystalline 5-azacytidine
characterized by data selected from the group consisting of: a PXRD pattern with peaks at about 9.4, 11.8, 12.1, 14.3 and 16.5±0.2 degrees two-theta; a PXRD pattern as depicted in FIG. 9; a solid-state $^{13}$C NMR spectrum having signals with chemical shifts at about 166.6, 154.3, and 93.9±0.2 ppm; a solid-state $^{13}$C NMR spectrum having signals with chemical shifts at about 166.6, 155.8, and 93.9±0.2 ppm; a solid-state $^{13}$C NMR spectrum as depicted in FIG. 10; a solid-state $^{13}$C NMR spectrum having chemical shift differences between the signal exhibiting the lowest chemical shift and another in the chemical shift range of 90 to 180 ppm of about 60.4 and 72.7° 0.1 ppm, a solid-state $^{13}$C NMR spectrum having chemical shift differences between the signal exhibiting the lowest chemical shift and another in the chemical shift range of 90 to 180 ppm of about 61.9 and 72.7±0.1 ppm, and combinations thereof.

18. The crystalline 5-azacytidine according to claim 17, characterized by data a PXRD pattern with peaks at about 9.4, 11.8, 12.1, 14.3 and 16.5±0.2 degrees two-theta.

19. The crystalline 5-azacytidine according to claim 18, characterized by a PXRD pattern as depicted in FIG. 9.

20. The crystalline 5-azacytidine according to claim 17, characterized by a solid-state $^{13}$C NMR spectrum as depicted in FIG. 10.

* * * * *